United States Patent [19]

Geiger et al.

[11] E Patent Number: Re. 32,015

[45] Reissued Date of Patent: Oct. 29, 1985

[54] PROCESS FOR THE MANUFACTURE OF INSULIN, ANALOGS AND DERIVATIVES THEREOF

[75] Inventors: Rolf Geiger, Frankfurt am Main; Rainer Obermeier, Hattersheim am Main, both of Fed. Rep. of Germany

[73] Assignee: Hoechst Aktiengesellschaft, Frankfurt am Main, Fed. Rep. of Germany

[21] Appl. No.: 22,852

[22] Filed: Mar. 22, 1979

Related U.S. Patent Documents

Reissue of:

[64] Patent No.: 4,014,861
Issued: Mar. 29, 1977
Appl. No.: 585,604
Filed: Jun. 10, 1975

[51] Int. Cl.[4] ..... C07C 103/52

[52] U.S. Cl. ..... 260/112.7

[58] Field of Search ..... 260/112.7

[56] References Cited

U.S. PATENT DOCUMENTS

| | | | |
|---|---|---|---|
| 3,883,496 | 5/1975 | Geiger | 260/112.7 |
| 3,883,500 | 5/1975 | Geiger et al. | 260/112.7 |
| 3,884,897 | 5/1975 | Geiger et al. | 260/112.7 |
| 3,907,763 | 9/1975 | Brandenbury et al. | 260/112.7 |
| 3,996,268 | 12/1976 | Carpenter et al. | 260/112.7 |

OTHER PUBLICATIONS

J. Am. Chem. Soc. 83 (1961), 1510–1511.
J. Am. Chem. Soc. 96 (1974), 5947–5949.

*Primary Examiner*—Frederick E. Waddell
*Attorney, Agent, or Firm*—Curtis, Morris & Safford

[57] ABSTRACT

A process for manufacture of insulin, analogs and derivatives thereof by treating an insulin compound wherein the A- and B-chains are linked by a bis-methionyl-carbonyl-bridge, with cyano bromide.

4 Claims, No Drawings

PROCESS FOR THE MANUFACTURE OF INSULIN, ANALOGS AND DERIVATIVES THEREOF

Matter enclosed in heavy brackets [ ] appears in the original patent but forms no part of this reissue specification; matter printed in italics indicates the additions made by reissue.

The present invention relates to a process for the manufacture of insulin, analogs and derivatives thereof.

The process of the invention comprises treating, in an acid medium, a compound of the general formula I (I)

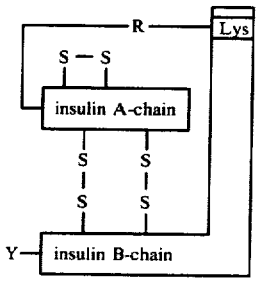

in which Y stands for hydrogen or an acyl group, and R stands for the radicals

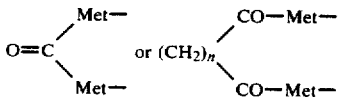

in which Met stands for the methionine radical, and n stands for an integer of 1 to 4, and one $CH_2$ group may also be substituted by oxygen, with cyano bromide.

According to Bioche. Biophys. Res. Commun, 55 (1973), page 60, insulin may be prepared from its chains by linking the α-amino group of the A-chain and the ε-amino group of the B-chain to each other by means of an α,α'-diamino-dicarboxylic acid, closing the disulfide bridge of the insulin corresponding to its formula by dehydrogenation, and finally splitting off the α,α'-diamino-dicarboxylic acid by Edman degradation.

According to said known process, the two chains of insulin could be combined for the first time with a high yield. The Edman degradation was also successful although a certain loss in yield could not be avoided.

According to the process of this invention, the two chains of insulin can now be combined with the same high yield. The yield obtained upon splitting off the bridging reagent is, however, higher. Moreover, this splitting-off reaction can be performed in a single operation. Whereas the Edman degradation requires two steps, i.e., the reaction of amino groups with phenylisothiocyanate and the splitting-off of the thiocarbamoyl compound, for example in trifluoroacetic acid, the splitting with cyano bromide proceeds without isolation of intermediate products. Furthermore, it leads to fewer byproducts than the Edman degradation, thus simplifying the purification of the reaction products.

Whilst in the Edman degradation the first amino acid of the B-chain, for example phenyl-alanine, is split off at the same time, unless the α-amino group is provided with a protective group, the α-amino group of the B-chain remains unaffected by the cyano bromide splitting reaction, though it may be advantageous for a smooth reaction course to protect this α-amino group as well.

The reaction mechanism for the manufacture of the compounds of formula I by successive linking of the bifunctional bridge member R to the A- and B-chains of insulin, respectively, has already been disclosed in the above-cited literature as well as in German Offenlegungsschrift No. 2,252,157.

For preparing the compounds of formula I, an insulin A-chain, the SH groups of which are blocked by one of the known S-protective groups, for example trityl, diphenyl-methyl, S-alkyl having 1 to 4 carbon atoms, picolyl, acetamido-methyl or sulfonate groups, is reacted with an excess reagent of the general formula II

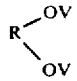

(II)

in which R is defined as above, and OV stands for the radical of an activated ester of the methionine component, for example of N-hydroxy-succinimide ester, nitrophenyl ester, trichlorophenyl ester, pentachlorophenyl ester, pentafluorophenyl ester or 1-hydroxy-benzetriazole ester.

The resulting compounds correspond to the general formula III

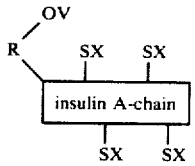

(III)

in which X stands for an S- protective group.

As solvents suitable for this reaction, dimethylsulfoxide (DMSO) or a dialkyl carboxylic acid amide, especially dimethylformamide (DMF) or phosphoric acid tris-dimethyl amide, are preferably used. The reaction is carried out at room temperature, but a slightly elevated temperature may also be employed.

In a corresponding manner, the compound of the general formula III is reacted with an insulin B-chain at a pH-value of about 8 to 11, or with the addition of a tertiary organic base, such as N-ethyl-morpholine in DMSO or DMF, and this reaction yields a compound of the general formula IV (IV)

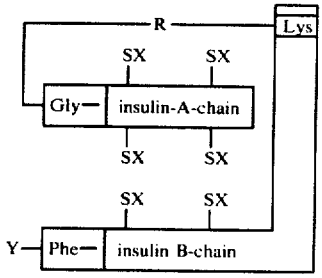

in which R and Y are defined as above. As the N-protective group (Y), for example tert.-butyloxycarbonyl (Boc)-, phthaloyl-or trifluoroacetyl groups are mentioned.

If Y stands for an N-protective group, the above reaction sequence may also be reversed, i.e., linkage with the B-chain is the first to be performed, followed by the linkage with the A-chain.

After the protective groups, if any, have been split off and, if necessary, the product has been purified by chromotography, the reaction product is dissolved in an 8M aqueous urea solution or water at a pH of 5 to 9. If X stands, for example, for —$SO_3H$, a 50- to 100-fold excess of thioglycol or 1 to 5 times the calculated amount of a trialkyl phosphine, for example tributyl phosphine, is added under a nitrogen atmosphere at 0°-60° C.; when the reduction is complete, the mixture is precipitated with acetone containing about 1°-10% acetic acid, the precipitate is centrifuged and washed several times with acetone containing about 1-10% acetic acid. Then, it is dissolved in the smallest possible amount of aqueous ammonia and diluted with 0.05 $(NH_4)HCO_3$, adjusted to pH 10-10.6, to reach a peptide concentration of from 0.01 to 1 mg/ml. The solution is then stirred overnight at 0°-20° C. in a slow air current. It is also possible to work at a lower pH-value, for example of 8-10, but then longer reaction times of up to about 150 hours are required. The methionine sulfur is generally not oxidized under these reactions conditions, but if necessary a scarcely volatile thio ether, for example methyl-phenyl sulfide or even methionine, is added. The pH-value is then adjusted to 4-5.5 with 1N acetic acid, and the resulting compound of formula I is lyophilized or evaporated to dryness in vacuo.

For purification purposes, the product is chromatographed in 1 to 2N acetic acid using Sephadex G 50® or G 75® in a column having a length of 1 to 2 m. The "insulin peak" (up to about 70%) is processed in the following manner, the product that has been combined in the wrong way (up to about 30%) beinb recycled to a recombination upon reduction.

The elimination of radical R from the compounds of formula I according to the invention is carried out by splitting it off by means of cyano bromide in an acid medium.

The compound of formula I is dissolved at a pH of from about 0 to 3 in an aqueous inorganic or organic acid, for example hydrochloric acid, sulfuric acid or phosphoric acid, furthermore formic acid, acetic acid, chloroacetic acid, trifluoroacetic acid, or even a sulfonic acid, for example benzene-or toluene-sulfonic acid, may be used. To increase the solubility of the compound of formula I, the organic acid may be used in a high concentration, for example from 40 to 90%, or water-miscible, organic solvents that are sufficiently stable toward acids, for example aliphatic alcohols having 1 to 4 carbon atoms, carboxylic acid amides, such as, for example N-methyl-pyrrolidine, dimethylformamide, dimethylsulfoxide or dioxan, are added to the solution. Then an excess amount of cyano bromide is added, the excess advantageously being from about 30 to 200 molecules of cyano bromide per methionine radical. The reaction is carried out at a temperature of 0°-35° C. and takes about 2 to 50 hours, depending on the temperature.

The reaction product is worked up, for example by distilling off the solvent in vacuo, or when a high-boiling solvent has been used, the water is distilled off first in vacuo and then the reaction product is precipitated with ether or ethyl acetate. The residue or precipitate is dissolved in a small amount of dilute acetic acid, and the solution is chromatographed on Sephadex G 50® or G 75®. Elution was performed with dilute acetic acid, the insulin-containing fractions are combined, and the pH is adjusted to 5.2, whereupon the insulin that has first precipitated in an amorphous form crystallizes within several hours.

The yield is about 40%, calculated on the insulin A- and B-chains used.

The crystallized insulin obtained according to the invention has a biological activity of 24 I.U./mg as evaluated by measuring the reduction of the blood sugar level on rabbits. The amino acid analysis corresponds to the calculated values.

In addition to insulin itself, the process of the invention also provides analogs and derivatives of insulin. Insulin analogs are understood to be compounds in which one or more amino acids are exchanged for other, preferably simpler, amino acids, moreover insulins having a modified, preferably shortened, chain length.

As already known in the literature, the following groups in the A-chain may be replaced: $Gln^{15}$ by Glu; $Ser^{12}$, $Tyr^{14}$, $Asn^{18}$ and $Asn^{21}$ by Ala; $Val^{10}$ by Leu or another hydrophobic amino acid; $Tyr^{19}$ by Phe.

In the B-chain, $Phe^1$, $Val^2$, $Asn^3$, $Gln^4$, $His^5$, $Ser^9$, $His^{10}$, $Thr^{27}$ and $Pro^{28}$ may be replaced by simpler amino acids, preferably by alanine. The amino acids 1 to 4 and 30 may also be eliminated. $Cys^{A7}$ and $Cys^{B7}$ may even be replaced by Ala.

Insulin derivatives are understood to be compounds which carry substituted functional groups, for example the α-amino group of the B-chain may be substituted by an acyl group as disclosed in German Offenlegungsschrift No. 2,042,299. The same applies to the above-defined insulin analogs.

Since the substitution of the α-amino group of the insulin B-chain by any group represented by Y is not critical for the biological activity, Y may stand not only for one of the N-protective groups usual in the peptide chemistry but also for any physiologically acceptable acyl group which, however, has to be limited in its size. For example, for aliphatic alkanoyl or alkyloxycarbonyl groups, this limit is about 6 carbon atoms, for a cycloalkanoyl group or the radical of an aromatic or heterocyclic carboxylic acid it is about 10 carbon atoms. Y may also stand for an aminoacyl group of naturally occuring α-amino groups or the D-enantiomers and ω-amino-carboxylic acids thereof having up to 6 carbon atoms, as well as of N-alkanoyl or N-alkyloxycarbonyl compounds having up to about 4 carbon atoms, a cycloalkanoyl group or a radical or an aromatic or heterocyclic carboxylic acid having up to about 7 carbon atoms.

Only such substituents are appropriate which do not decrease the biological activity of the insulins or decrease it to only a minor extent. Biological activity not only includes a lowering of the blood sugar level but also, for example the ability of these compounds to serve as haptens for antibodies if present.

The insulin or the analogs and derivatives thereof obtained according to the process of the invention are used in the same manner and dosage as that of the material recovered from the pancreas for the treatmet of diabetes mellitus in human beings, or they are generally used, as insulin is, to lower the blood sugar level, for example in order to produce shock.

The insulin A- and B-chain are prepared according to one of the numerous methods described in the art. To demonstrate the process of the invention, it is simpler to start from natural chains which can be easily obtained from insulin by sulfitolysis. The insulin chains prepared by synthesis behave like the natural material. This applies also to modified chains, provided these chains still possess the decisive structural characteristics for the biolgoical activity of the insulin prepared therefrom.

The reagents of formula II are obtained, for example by reacting methionine alkyl esters, preferably methyl ester, with a derivative of carbonic acid or activated dicarboxylic acids, saponifying the alkyl ester and converting it into an activated ester. The following reaction schemes illustrate

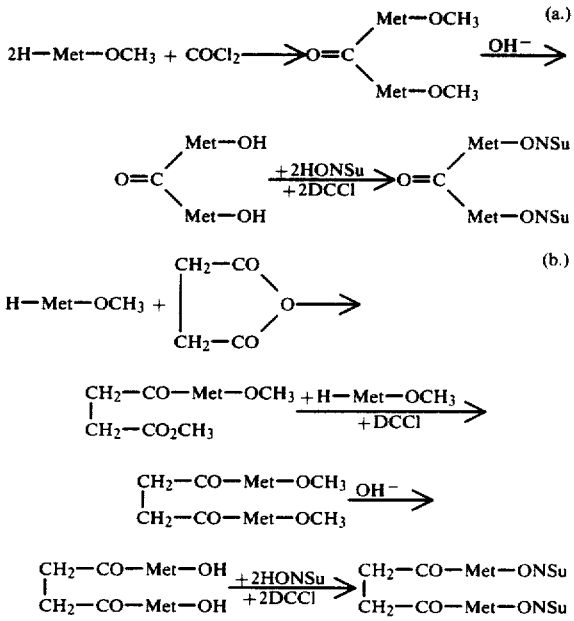

EXAMPLE 1

Preparation of bridge reagents a. Succinic acid bis-L-methionine methyl ester 4.0 grams of L-methionine methyl ester hydrochloride were dissolved in 60 ml of dimethyl formamide while adding 2.8 ml of triethylamine. After addition of 2.0 g of succinic acid anhydride, the mixture was stirred for 2 hours, another 4.0 g of L-methionine methyl ester hydrochloride and 2.8 ml of triethylamine were added and, after 30 minutes, combined with 2.7 g of 1-hydroxybenzotriazle and 4.4 g of dicyclohexyl carbodiimide. The mixture was stirred for 4 hours, concentrated in vacuo to a small volume, and the residue was dissolved in ethyl acetate. After the solution had been washed with aqueous $KHSO_4$, $NaHCO_3$ and water, it was dried over $Na_2SO_4$, and the ethyl acetate was distilled off in vacuo. The residue was dissolved in toluene, filtered and combined with petroleum ether until the mixture began to become turbid. Upon standing overnight (at −20° C.), 4.8 g of an amorphous material precipitated.

b. Succinic acid bis-L-methienine 3.5 grams of bis-methyl ester as obtained sub (a) were dissolved in 80 ml of a 1:1-mixture of dioxan and water. The solution was saponified at pH 11.5–12 with 8.9 ml of 2N NaOH; when the reaction was complete, the same amount of 2N HCl was added, and the mixture was dried in vacuo. The residue was taken up in isopropanol, NaCl was separated by filtration, and after isopropanol had been distilled off, the product was recrystallized twice from ethyl acetate. Yield: 2.8 g, m.p. 125°–135° C.

To characterize the acid, the dicyclohexyl amine salt was prepared and recrystallized from a 1:1 mixture of acetonitrile and isopropanol. Melting point: 184°–185° C. The elemental analysis corresponds to the calculated values.

c. Succinic acid bis-L-methionine N-hydroxy-succinimide ester

In the usual way, the corresponding bis-N-hydroxy-succinimide ester was prepared from 4.0 g of the acid obtained according to (b), 2.4 g of N-hydroxy-succinimide and 4.2 g of DCCI in dioxan. The dicyclohexyl urea which had precipitated was separated by filtration, and the solvent was distilled off in vacuo. The deactivated ester was of resinous nature and could be used without further purification.

d. Glutaric acid bis-L-methionine N-hydroxy-succinimide ester

This compound was prepared in a manner analogous to (a)–(c). In this case, too, the activated ester was of resinous nature and was used without further purification. The melting point of the acid was 66°–70° C., that of the dicyclohexyl amine salt ranged from 187° to 189° C. The elemental analysis corresponds to the calculated values.

EXAMPLE 2

Bovine insuline a. Bovine insulin A-chain tetrasulfonate

This compound was prepared from bovine insulin in known manner, for example according to Z. Naturforsch. 18b (1963), page 978.

b. $N^{B1}$-trifluoroacetyl-B-chain disulfonate (bovine)

This compound was also prepared in the usual way by sulfitolysis of $N^{B1}$-trifluoroacetyl insulin (bevine). The latter starting product was obtained as follows:

$N^{\alpha A1}$, $N^{\epsilon B29}$-bis-Boc-insulin prepared according to Hoppe Seyler's Z. Physiol. Chem. 352 (1971), page 1487, was dissolved in dimethylformamide, and the solution was reacted with about 5 equivalents of trifluoroacetic acid methyl ester, thus yielding $N^{\alpha A1}$, $^{\epsilon}N^{B29}$-bis-Boc-$N^{\alpha B1}$-trifluoroacetyl insulin (bovine). After the Boc-groups had been split off by a 45-minute treatment with trifluoroacetic acid, the product was purified by partition chromatography using Sephadex LH-20® in a system of n-butanol/glacial acetic acid/-water(2:1:10).

c. Bovine insulin

The pH-vaue of a solution of 2.82 g of the A-chain tetrasulfonate prepared sub (a) in 200 ml of dimethyl sulfoxide was adjusted to about 9 by adding 1.11 ml of N-ethyl-morpholine, and the mixture was stirred with 1.8 g of the N-hydroxy-succinimide ester prepared according to Example 1 (c). After 20 hours, the product was precipitated with a 10:1 mixture of ether and methanol. The precipitate was then dissolved in 200 ml of dimethylsulfoxide 3.45 g of the $N^{B1}$-trifluoroacetyl B-chain disulfonate prepared sub (b) and 1.1 ml of N-ethyl-morpholine were added, and the mixture was stirred for 6 to 24 hours at room temperature. The product was then precipitated with a 10:1 mixture of ether and methanol. Yield: 5.3 g.

Upon chromatography in a column using Sephadex G 50® (column size: 4 m in length and 4 cm in diameter) in 0.05M $(NH_4)HCO_3$ buffer solution of pH 8.5 to 9 and lyophilization, the product was dissolved in 0.25 l of water at pH 8.6. 50 ml of thioglycol were added, the mixture was stored for 6 hours under a nitrogen atmosphere, then precipitated with 10 to 20 times its amount of acetone containing about 1-10% acetic acid, centrifuged and washed with acetone containing about 1-10% acetic acid until free of thiolgycol. The product was then dissolved in a small amount of 1N $NH_3$, diluted to 25 l, the pH-value was adjusted to 9, and the solution was stirred for about 100 hours in the presence of 1 g of methylphenyl sulfide in a slight air stream at room temperature.

Under these conditions, the trifluoroacetyl group was split off at the same time. The pH was adjusted to 5.5 with acetic acid, and the solution was lyophilized.

The residue ws dissolved in 50 ml of 10% acetic or formic acid and chromatographed through a column, sized 4×200 cm, using Sephadex G 50® or G 75®, fine. Partition chromatography using Sephadex LH 20® in a system of n-butanol/acetic acid/water (2:1:10) also allowed good purification (column size: 4×100 to 4×200 cm). The column had been calibrated with cross-linked insulin. After a preliminary peak had passed through, the main fraction was reduced according to J. Amer. Chem. Soc. 93 (1971), page 3080, using 1,4-dithio-threitol in liquid $NH_3$ or tributyl-phosphine in dilute aqueous $NH_3$, at pH 8-10, and oxidized in water at pH 9 in the manner described above.

To split off the cross-linking reagent, the product was dissolved in 100 ml of 70% formic acid, 15 g of BrCN were added and after 15 hours, the solution was concentrated to a small volume. The product was immediately introduced into a column (100×4 cm), that was packed with Sephadex G 50®, and eluted with 1% acetic acid. The fractions containing insulin were combined, concentrated in vacuo to a volume of about 40 ml, the pH thereof was adjusted to 5.2 by adding a small amount of $ZnCl_2$, and the substance was allowed to stand for 1 day at room temperature. The resulting crystals were separated by centrifuging the material from non crystallizing material, and crystallization was repeated. Yield: 2.3 g (38%). The biological activity of the insulin was 24 I.U./mg.

We claim:

1. A method for making an insulin compound of the formula

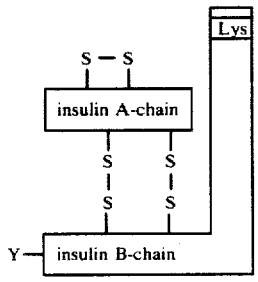

and biologically-active analogs thereof in which one or more amino acids have been exchanged for other, preferably simpler, amino acids or in which the chains are modified, preferably shortened, and in which Y is hydrogen or acyl, which method comprises treating a compound of the formula

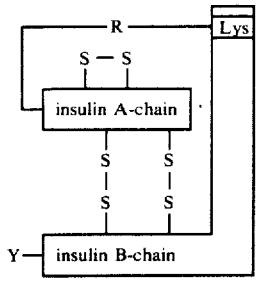

or an analog thereof as hereinbefore defined, wherein R is

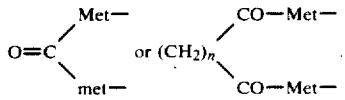

Met is methionine, n is an integer from 1 to 4, and one —$(CH_2)$— may be replaced by oxygen, with cyano bromide in an acid medium.

2. An insulin compound of the formula

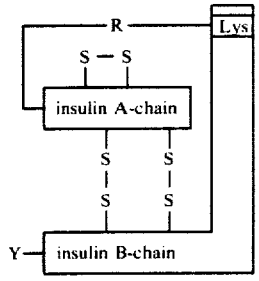

wherein Y is hydrogen or acyl, R is

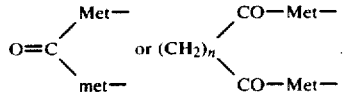

Met is methionine, n is an integer from 1 to 4, and one —$(CH_2)$— group may be replaced by oxygen, and biologically-active analogs thereof in which one or more amino acids have been exchanged for other, preferably simpler, amino acids or in which the chains are modified, preferably shortened.

*3. A method for making an insulin compound of the formula*

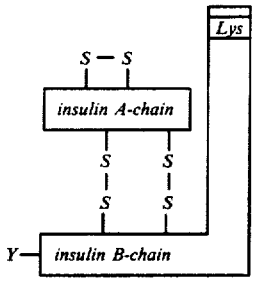

*and biologically-active analogs thereof in which one or more amino acids have been exchanged for other, preferably simpler, amino acids or in which the chains are modified preferably shortened, and in which Y is hydrogen or acyl, which method comprises reacting an insulin A-chain fragment, an insulin B-chain fragment, and a bridging agent of the formula*

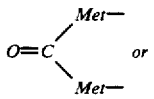

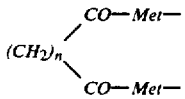

*Met is methionine, n is an integer from 1 to 4, and one —(CH₂)— may be replaced by oxygen, and OV is an activated ester of methionine, to form a compound of the formula*

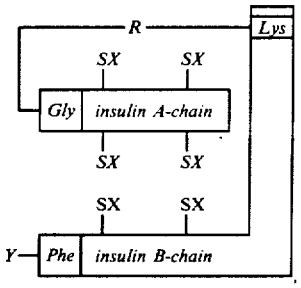

*oxidizing the —SX groups to form a compound of the formula*

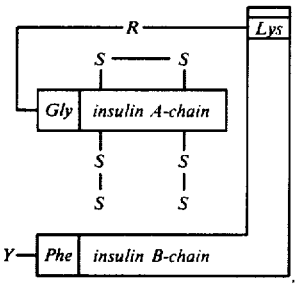

*and then treating said last-mentioned compound with cyano bromide in an acid medium.*

*4. A method for making an insulin compound which comprises reacting an A-chain fragment of insulin, a B-chain fragment of insulin, and an activated ester of a bridging agent of the formula*

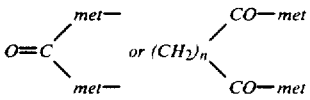

*where met is methionine and n is an integer from 1 to 4, oxidizing the resulting compound to form disulfide cross-links between the A-chain and B-chain, and then treating the product with cyano bromide in an acid medium.*

* * * * *

UNITED STATES PATENT AND TRADEMARK OFFICE

CERTIFICATE OF CORRECTION

PATENT NO. : RE 32,015

DATED : October 29, 1985

INVENTOR(S) : Geiger et al.

It is certified that error appears in the above-identified patent and that said Letters Patent is hereby corrected as shown below:

Column 8, lines 25 and 50, column 10, lines 37, 42 and 43, change "met" to --Met-- (each occurrence).

Signed and Sealed this

*Fifteenth* Day of *April 1986*

[SEAL]

*Attest:*

DONALD J. QUIGG

*Attesting Officer*

*Commissioner of Patents and Trademarks*